United States Patent [19]
Gallenkamp et al.

[11] Patent Number: 4,820,847
[45] Date of Patent: Apr. 11, 1989

[54] PROCESS FOR THE PREPARATION OF 4-SUBSTITUTED 1-ARYL-5-AMINO-PYRAZOLES

[75] Inventors: Bernd Gallenkamp, Wuppertal; Heinz-Jürgen Wroblowsky, Langenfeld; Dietmar Bielefeldt, Ratingen, all of Fed. Rep. of Germany

[73] Assignee: Bayer Aktiengesellschaft, Leverkusen, Fed. Rep. of Germany

[21] Appl. No.: 92,747

[22] Filed: Sep. 3, 1987

[30] Foreign Application Priority Data

Sep. 12, 1986 [DE] Fed. Rep. of Germany ....... 3631003

[51] Int. Cl.$^4$ .................. C07D 231/44; C07D 401/04
[52] U.S. Cl. ..................................... 548/362; 546/279
[58] Field of Search ........................ 548/362; 546/279

[56] References Cited
FOREIGN PATENT DOCUMENTS 0138149  4/1985  European Pat. Off. ............ 548/362
0167028  1/1986  European Pat. Off. .
2141700  2/1973  Fed. Rep. of Germany ...... 548/362
3402308  1/1985  Fed. Rep. of Germany ...... 548/362
3447211  6/1986  Fed. Rep. of Germany ...... 548/362

OTHER PUBLICATIONS

Cehm. Ber. 107, 1545–1554 (1974) Synthese und Reaktionen von 1,2-Bis(Dialkylamino)Athylenen.

Primary Examiner—Robert W. Ramsuer
Attorney, Agent, or Firm—Sprung Horn Kramer & Woods

[57] ABSTRACT 4-susbstituted 1-aryl-5-amino-pyrazoles of the formula $$\begin{array}{c} R^1 \diagup\!\!\!\diagdown S-R^2 \\ N\diagdown\!\!\!\diagup \diagdown NH_2 \\ | \\ Ar \end{array}$$

in which
$R^1$ represents hydrogen or alkyl,
$R^2$ represents alkyl or halogenoalkyl, and
Ar represents in each case polysubstituted phenyl or polysubstituted pyridyl, some of which are known, are obtained when an arylhydrazine hydrohalide of the formula $$AR-NH-NH_2 \times HHal$$

in which
Hal represents halogen, and
Ar has the abovementioned meaning,
is reacted with an acrylonitrile derivative of the formula $$\begin{array}{c} R^3 \quad R^1 \quad CN \\ \diagdown \;\;|\;\; \diagup \\ N-C=C \\ \diagup \quad\quad \diagdown \\ R^4 \quad\quad S-R^2 \end{array}$$

in which
$R^1$ and $R^2$ have the abovementioned meaning, and
$R^3$ and $R^4$, independently of one another, in each case represent alkyl or phenyl, or
$R^3$ and $R^4$, together with the nitrogen atom to which they are bound, represent a saturated heterocyclic ring,
at temperatures between 60° C. and 90° C.

9 Claims, No Drawings

PROCESS FOR THE PREPARATION OF 4-SUBSTITUTED 1-ARYL-5-AMINO-PYRAZOLES

The invention relates to a new process for the preparation of 4-substituted 1-aryl-5amino-pyrazoles, some of which are known and which have insecticidal and herbicidal properties.

It has already been disclosed that certain 4-substituted 1-aryl-5-amino-pyrazoles are obtained when 4-unsubstitued 1-aryl-5-amino-pyrazoles are reacted with electrophilic reagents (cf. DE-OS (German Published Specification) No. 3,402,308). The 4-unsubstituted 1-aryl-5-amino-pyrazoles used as precursors are generally prepared in this case from suitably substituted acrylonitrile derivatives and appropriate arylhydrazines, if appropriate via intermediates which must be isolated intermediately (cf., for example, DE-OS (German Published Specification) No. 3,402,308 and DE-OS (German Published Specification) No. 2,141,700).

The disadvantages of a multistage reaction procedure are obvious, in particular when it is necessary to employ poorly accessible and thus expensive starting compounds—such as, in this case, suitably substituted arylhydrazines—as early as the first stage.

It has furthermore been disclosed that certain 4-substituted 1-aryl-5-amino-pyrazoles can also be obtained when appropriate arylhydrazines are cyclized directly using suitably substituted acrylonitrile derivatives under certain reaction conditions (cf. DE-OS (German Published Specification) No. 3,402,308).

However, this process is only suitable for certain substituents to be introduced into the 4-position. Thus, for example, α-alkylthio- or α-halogenoalkylthio-substituted β-dimethylamino-acrylonitriles cannot be cyclized directly using arylhydrazines without the starting materials and/or final products partially decomposing at the high temperatures necessary, particularly when the reactivity of the arylhydrazines involved is greatly reduced by several electronegative substituents. The use of α-alkylthio- or α-halogenoalkylthio-β-alkoxy-substituted acrylonitriles fails if only because these starting compounds are difficult to prepare. The 4-alkylthio- and 4-halogenoalkylthio-5-amino-1-arylpyrazoles having several generally electronegative substituents in the aryl part (cf. DE-OS (German Published Specification) No. 3,402,308 or the as yet unpublished German Patent Application P No. 3,517,843 of 17.05.1985) which are important, in particular, as insecticides and herbicides are therefore not accessible in satisfactory yield and purity by this route.

It has now been found that the 4-substituted 1-aryl-5-amino-pyrazoles of the general formula (I),

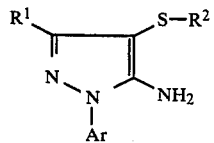

in which
R$^1$ represents hydrogen or alkyl,
R$^2$ represents alkyl or halogenoalkyl, and
Ar represents in each case polysubstituted phenyl or pyridyl, some of which are known, are obtained when arylhydrazine hydrohalides of the formula (II),

in which
Hal represents halogen, and
Ar has the abovementioned meaning, are reacted with acrylonitrile derivatives of the formula (III),

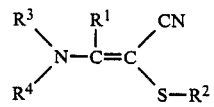

in which
R$^1$ and R$^2$ have the abovementioned meaning, and
R$^3$ and R$^4$, independently of one another, in each case represent alkyl or phenyl, or
R$^3$ and R$^4$, together with the nitrogen atom to which they are bound, represent a saturated heterocyclic ring, at temperatures between 60° C. and 90° C., if appropriate in the presence of a diluent.

It must be regarded as exceptionally surprising that the reaction according to the invention can be carried out in high yield under these reaction conditions since it was to be expected, from the state of the art, that arylhydrazines which are polysubstituted by electronegative substituents only undergo the desired ring closure at significantly higher temperatures (cf., for example, DE-OS (German Published Specification) No. 2,141,700 or DE-OS (German Published Specification) No. 3,226,513 or EP No. 138,149), and since the analogous reaction of the acrylonitrile derivatives of the formula (III) with free arylhydrazine bases in place of the arylhydrazine hydrohalides of the formula (II) which can be used according to the invention does not lead to notable yields of the desired products of the formula (I).

The formula (I) provides a general definition of the 4-substituted 1-aryl-5-amino-pyrazoles which can be prepared with the aid of the process according to the invention. Compounds of the formula (I) which can preferably be prepared are those in which
R$^1$ represents hydrogen, or straight-chain or branched alkyl having 1 to 6 carbon atoms,
R$^2$ represents straight-chain or branched alkyl having 1 to 6 carbon atoms or straight-chain or branched halogenoalkyl having 1 to 4 carbon atoms and 1 to 9 identical or different halogen atoms, and
Ar represents phenyl which is disubstituted to pentasubstituted, the substituents being identical or different, or 2-pyridyl, 3-pyridyl or 4-pyridyl which is in each case disubstituted to tetrasubstituted, the substituents being identical or different and suitable substituents in each case being: cyano, nitro, halogen, in each case straight-chain or branched alkyl, alkoxy or alkoxycarbonyl in each case having up to 4 carbon atoms, in addition in each case straight-chain or branched halogenoalkyl or halogenoalkoxy in each case having up to 4 carbon atoms and up to 9 identical or different halogen atoms, or an —S(O)$_m$—R$^5$ radical,
where
R$^5$ represents amino or in each case straight-chain or branched alkyl, alkylamino, dialkylamino or halogenoalkyl in each case having up to 4 carbon atoms in the individual alkyl parts and, in the case of halogenoalkyl, having up to 9 identical or different halogen atoms, and m represents a number 0, 1 or 2.

Compounds of the formula (I) which can particularly preferably be prepared are those in which $R^1$ represents hydrogen, methyl, ethyl, n- or i-propyl, or n-, i-, s- or t-butyl, $R^2$ represents methyl, ethyl, n- or i-propyl, n-, i-, s- or t-butyl, trifluoromethyl, trichloromethyl, difluorochloromethyl or dichlorofluoromethyl, fluoromethyl or difluoromethyl, and Ar represents phenyl which is disubstituted to pentasubstituted, the substituents being identical or different, or 2-pyridyl or 4-pyridyl which is in each case disubstituted to tetrasubstituted, the substituents being identical or different and suitable substituents in each case being: cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, dichlorofluoromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or an —S(O)$_m$—R$^5$ radical, where $R^5$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, and m represents a number 0, 1 or 2.

If, for example, 2,6-dichloro-4-trifluoromethylphenylhydrazine hydrochloride and 2-trifluoromethylthio-3-dimethylaminoacrylonitrile are used as starting materials, the course of the reaction of the process according to the invention may be represented by the following equation:

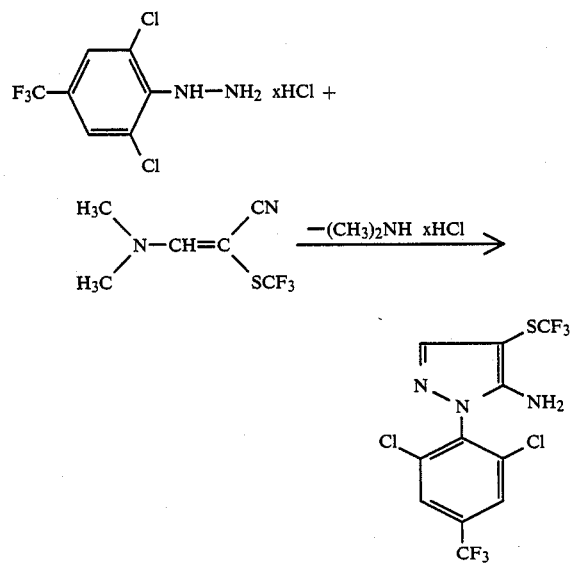

Formula (II) provides a general definition of the arylhydrazine hydrohalides which are required as starting materials for carrying out the process according to the invention. In this formula (II), Ar preferably represents those radicals which have already been mentioned in connection with the description of the substances of the formula (I) according to the invention as being preferred for this substituent. Hal preferably represents chlorine or bromine.

The arylhydrazine hydrohalides of the formula (II) are known or can be obtained analogously to known processes, for example by mixing the known arylhydrazines of the formula (IIa) (cf., for example, EP No. 138,149 or DE-OS (German Published Specification) No. 3,402,308 or DE-OS (German Published Specification) No. 3,447,221),

in which

Ar has the abovementioned meaning, with hydrohalic acids of the formula (IV),

in which

Hal has the abovementioned meaning, if appropriate in the presence of a diluent, such as, for example, ethanol, and the diluent and any hydrohalic acid which may be present in excess are removed again using conventional methods (distillation or filtration).

It is also possible to prepare the arylhydrazine hydrohalides of the formula (II) directly in the reaction batch by employing the corresponding free arylhydrazine bases of the formula (IIa) as starting compound and adding at least equimolar amounts of hydrohalic acid of the formula (IV) to the reaction batch.

Formula (III) provides a general definition of the acrylonitrile derivatives which are furthermore required as starting materials for carrying out the process according to the invention. In this formula (III), $R^1$ and $R^2$ preferably represent those radicals which have already been mentioned in connection with the description of the substances of the formula (I) according to the invention as being preferred for these substituents. $R^3$ and $R^4$, independently of one another, preferably represent methyl, ethyl or phenyl or, together with the nitrogen atom to which they are bound, represent a pyrrolidinyl, piperidinyl or morpholinyl radical.

The acrylonitrile derivatives of the formula (III) are known (cf., for example, Chem. Ber. 107, 1545–1554 [1974] or Tetrahedron Lett. 22, 4259–4262 [1981]) or can be obtained analogously to known processes, for example by reacting the alkylthio- or halogenoalkylthio-acetonitriles of the formula (V),

in which $R^2$ has the abovementioned meaning, the majority of which are known, with generally known aminoacetals of the formula (VI),

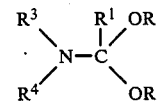

in which

R represents alkyl, in particular methyl, and

R¹, R³ and R⁴ have the abovementioned meaning, at temperatures between 0° C. and 60° C., if appropriate in the presence of a diluent or alternatively without a diluent.

Suitable diluents for carrying out the process according to the invention are polar organic solvents or aqueous mixtures. These include, in particular, alcohols, such a methanol, ethanol or propanol, nitriles, such as acetonitrile or propionitrile, amides, such as dimethylformamide, dimethylacetamide, N-methylformanilide, N-methylpyrrolidone or hexamethylphosphoric triamide, or sulphoxide, such as dimethyl sulphoxide, or mixtures thereof with water.

When carrying out the process according to the invention, the reaction temperatures can be varied within a relatively wide range. In general, the reaction is carried out at temperatures between 60° C. and 90° C., preferably at temperatures between 70° C. and 80° C.

To carry out the process according to the invention, 1 to 1.5 moles, preferably equimolar amounts, of the acrylonitrile derivative of the formula (III) are generally employed per mole of arylhydrazine hydrohalide of the formula (II). The reaction mixture is stirred for several hours at the reaction temperature necessary and worked up by conventional methods, for example by taking the reaction mixture up in dichloromethane after removal of the solvent by distillation, removing any impurities or by-products by washing with water, and drying and concentrating the organic phase in vacuo. The products of the formula (I) thus obtainable are characterized with the aid of the melting point or, in the case of noncrystallizing compounds, with the aid of the proton nuclear magnetic resonance spectrum.

The majority of the compounds which can be prepared according to the invention are known as herbicides (cf. DE-OS (German Published Specification) No. 3,402,308) and, in addition, as good insecticides (cf. our own as yet unpublished German Patent Application P No. 3,517,843 of 17.05.1985).

PREPARATION EXAMPLES

Example 1

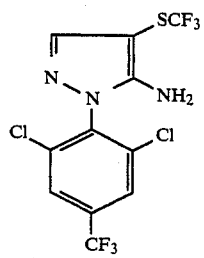

2 ml (0.07 mol) of concentrated hydrochloric acid are added dropwise to a solution of 1.69 g (0.01 mol) of 2-trifluoromethylthio-3-dimethylaminoacrylonitrile and 2.45 g (0.01 mol) of 2,6-dichloro-4-trifluoromethylphenylhydrazine in 20 ml of ethanol, and the mixture is heated at the reflux temperature for 78 hours. For work-up, the reaction mixture is concentrated in vacuo, the residue is taken up in dichloromethane, washed with water and dried over sodium sulphate, and the solvent is removed in vacuo.

3.5 g (88% of theory) of 5-amino-1-(2,6-dichloro-4-trifluoromethylphenyl)-4-trifluoromethylthiopyrazole of melting point 113° C.–117° C. are obtained.

Preparation of the starting compound

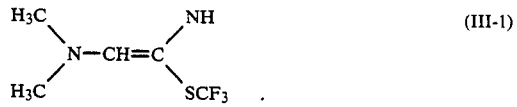

19.74 g (0.14 mol) of trifluoromethylthioacetonitrile (cf. J. Org. Chem. 37, 130–1346 [1972]) and 133 g (0.14 mol) of dimethylformamide dimethylacetal are stirred at 150° C. for 3 hours and subsequently freed of volatile components in vacuo.

25.5 g (100% of theory) of 3-dimethylamino-2-trifluoromethylthio-acrylonitrile of refractive index $n_D^{20}=1.4916$ are obtained.

Example 2

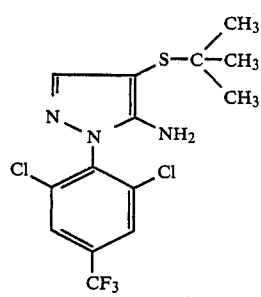

9.2 g (0.05 mol) of 1-t-butylthio-2-dimethyl-aminoacrylonitrile and 14.1 g (0.05 mol) of 2,6-dichloro-4-trifluoromethylphenylhydrazine hydrochloride are refluxed for 2 days in 250 ml of ethanol. For work-up, the mixture is concentrated in vacuo, the residue is taken up in dichloromethane, washed with water and saturated aqueous sodium chloride solution and dried over magnesium sulphate, the solvent is removed in vacuo, and the residue is crystallized by triturating with petroleum ether.

12.6 g (66% of theory) of 5-amino-4-t-butylthio-1-(2,6-dichloro-4-trifluoromethylphenyl)-pyrazole of melting point 129° C. are obtained.

Preparation of the starting compound

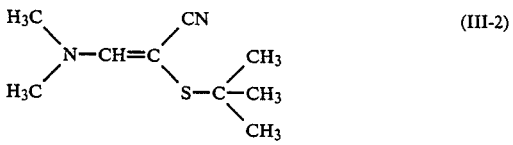

49.6 g (0.384 mol) of t-butylthioacetonitrile and 91.5 g (0.769 mol) of dimethylformamide dimethylacetal are stirred for 15 hours at room temperature, concentrated in vacuo and fractionated in a high vacuum.

25.2 g (36% of theory) of 1-t-butylthio-2-dimethylaminoacrylo-nitrile of boiling point 138° C.–145° C. at 2 mbar are obtained. ¹H-NMR (CDCl₃/TMS): δ=1.29; 3.17; 6.84 ppm.

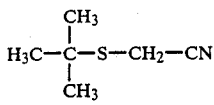

45.1 g (0.5 mol) of t-butyl mercaptan are added dropwise to 11.5 g (0.5 mol) of sodium in 300 ml of methanol at room temperature. When the addition is complete, the mixture is stirred for a further 30 minutes at room temperature, 35.7 g (0.5 mol) of chloroacetonitrile are then added dropwise, and the mixture is heated for 3 hours at the reflux temperature. For work-up, the mixture is concentrated, precipitated sodium chloride is filtered off, and the residue is fractionated in vacuo.

49.3 g (76% of theory) of t-butyl-thioacetonitrile of boiling point 74° C.–76° C. at 8 mbar are obtained.

The following 4-substituted 1-aryl-5-amino-pyrazoles of the general formula (I) are obtained in a corresponding fashion and according to the general instructions for the preparation

TABLE 1

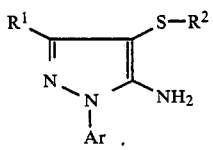

| Example No. | $R^1$ | $R^2$ | Ar | Melting point [°C.] |
|---|---|---|---|---|
| 3 | H | $C_2H_5$— | ![3,5-dichloro-4-CF3-phenyl] Cl, Cl, CF3 | 81–82 |
| 4 | H | $(CH_3)_2CH$—$CH_2$— | ![3,5-dichloro-4-CF3-phenyl] Cl, Cl, CF3 | 78 |

The following precursors of the general formula (III) are obtained in a corresponding fashion and according to the general instructions for the preparation

TABLE 3

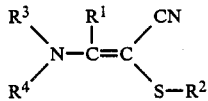

| Example No. | $R^1$ | $R^2$ | $-\underset{R^4}{\overset{R^3}{N}}-$ | Boiling point |
|---|---|---|---|---|
| III-3 | H | $C_2H_5$— | $-N(CH_3)_2$ | m.p 145–148° C./ 8 mbar |
| III-4 | H | $(CH_3)_2CH$—$CH_2$— | $-N(CH_3)_2$ | m.p 142° C./ 1 mbar |
| III-5 | H | $C_2H_5\!\!\diagdown\!\!\!\!CH\!\!-\!\!\diagup H_3C$ | $-N(CH_3)_2$ | m.p 134–140° C./ 1 mbar |

What is claimed is:

1. A process for the preparation of a 4-substituted 1-aryl-5-amino-pyrazole of the formula

in which
   $R^1$ represents hydrogen or alkyl,
   $R^2$ represents alkyl or halogenoalkyl, and
   Ar represents polysubstituted phenyl or polysubstituted pyridyl,
wherein a arylhydrazine hydrohalide of the formula $$Ar-NH-NH_2 \times HHal$$

in which
   Hal represents halogen, and
   Ar has the abovementioned meaning,
is reacted with an acrylonitrile derivative of the formula $$\underset{R^4}{\overset{R^3}{\diagdown}}N-\underset{\phantom{R^1}}{\overset{R^1}{\underset{|}{C}}}=C\underset{S-R^2}{\overset{CN}{\diagup}}$$

in which
   $R^1$ and $R^2$ have the abovementioned meaning, and
   $R^3$ and $R^4$, each independently represent alkyl or phenyl, or
   $R^3$ and $R^4$, together with the nitrogen atom to which they are bound, represent a saturated heterocyclic ring,
at temperatures between 60° C. and 90° C.

2. A process according to claim 1, wherein
   $R^1$ represents hydrogen, or straight-chain or branched alkyl having 1 to 6 carbon atoms or straight-chain or branched halogenoalkyl having 1 to 4 carbon atoms and 1 to 9 identical or different halogen atoms, and
   Ar represents phenyl which is disubstituted to pentasubstituted, the substituents being identical or different, or 2-pyridyl, 3-pyridyl or 4-pyridyl which is in each case disubstituted to tetrasubstituted, the substituents being identical or different and said substituents in each case being selected from the group consisting of cyano, nitro, halogen, in each case straight-chain or branched alkyl, alkoxy or alkoxycarbonyl in each case having up to 4 carbon atoms, in addition in each case straight-chain or branched halogenoalkyl or halogenoalkoxy in each case having up to 4 carbon atoms and up to 9 identical or different halogen atoms, and an $-S(O)_m-R^5$ radical,
wherein
   $R^5$ represents amino or in each case straight-chain or branched alkyl, alkylamino, dialkylamino or halogenoalkyl in each case having up to 4 carbon atoms in the individual alkyl parts and, in the case of halogenoalkyl, having up to 9 identical or different halogen atoms, and m represents a number 0, 1 or 2.

3. A process according to claim 1, wherein $R^1$ represents hydrogen, methyl, ethyl, n- or i-propyl, or n-, i-, s- or t-butyl, $R^2$ represents methyl, ethyl, n- or i-propyl, n-, i-, s- or t-butyl, trifluoromethyl, trichloromethyl, difluorochloromethyl, fluoromethyl or difluoromethyl, and Ar represents phenyl which is disubstituted to pentasubstituted, the substituents being identical or different, or 2-pyridyl or 4-pyridyl which is in each case disubstituted to tetrasubstituted, the substituents being identical or different, said substituents being selected from the group consisting of cyano, nitro, fluorine, chlorine, bromine, iodine, methyl, ethyl, n- and i-propyl, n-, i-, s- and t-butyl, methoxy, ethoxy, methoxycarbonyl, ethoxycarbonyl, trifluoromethyl, trichloromethyl, difluorochloromethyl, dichloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluoroethoxy, difluorodichloroethoxy, trifluorochloroethoxy, trifluorodichloroethoxy, pentachloroethoxy and an $-S(O)_m-R^5$ radical, wherein $R^5$ represents amino, methylamino, ethylamino, dimethylamino, diethylamino, fluorodichloromethyl, difluoromethyl, tetrafluoroethyl, trifluorochloroethyl, trifluoromethyl, methyl or ethyl, and m represents a number 0, 1 or 2.

4. A process according to claim 1, wherein the reaction is carried out at temperatures between 70° C. and 80° C.

5. A process according to claim 1, wherein 1 to 1.5 moles of said acrylonitrile derivative is employed per mole of said arylhydrazine hydrohalide.

6. A process according to claim 1, wherein equimolar amounts of said arylhydrazine hydrohalide and said acrylonitrile derivative are employed.

7. A process according to claim 1, wherein the process is carried out in the presence of a polar organic solvent.

8. A process according to claim 1, wherein the reaction is carried out in the presence of a diluent.

9. A process according to claim 7, wherein the reaction is carried out in the presence of a mixture of a polar organic solvent and water.

* * * * *